United States Patent [19]

Schwarzberg

[11] 4,235,869
[45] Nov. 25, 1980

[54] ASSAY EMPLOYING A LABELED FAB-FRAGMENT LIGAND COMPLEX

[75] Inventor: Moshe Schwarzberg, Sunnyvale, Calif.

[73] Assignee: Syva Company, Palo Alto, Calif.

[21] Appl. No.: 906,388

[22] Filed: May 16, 1978

[51] Int. Cl.² ............... G01N 21/00; G01N 31/00; G01N 31/14; G01N 33/16
[52] U.S. Cl. ............... 424/8; 23/230 B; 250/302; 424/1; 424/12; 424/13; 435/7
[58] Field of Search ............... 424/1, 8, 12, 13; 250/302; 23/230 B; 435/7

[56] References Cited

U.S. PATENT DOCUMENTS

| | | | |
|---|---|---|---|
| 3,935,074 | 1/1976 | Rubenstein | 195/103.5 |
| 3,996,345 | 12/1976 | Ullman | 424/12 |
| 3,998,943 | 12/1976 | Ullman | 424/12 |
| 4,104,029 | 8/1978 | Maier | 424/8 X |

OTHER PUBLICATIONS

Ternynck et al., Ann. Immunol. (Inst. Pasteur), vol. 127 C 1976 pp. 197–208.
Weir (Ed.), Handbook of Exptl. Immunology, Blackwell Sci. Pub. London, 2nd ed., 1973, pp. 14.19–14.25.
Carrico, et al., Anal. Biochem. vol. 72, 1972 pp. 271–282, 283–292.
Forsum, J. of Immuno. Methods, vol. 2, 1972 pp. 183–195.

Primary Examiner—Anna P. Fagelson
Attorney, Agent, or Firm—Bertram I. Rowland

[57] ABSTRACT

Methods and compositions are provided for improved protein binding assays by preparing compositions having indirectly labeled ligands substantially free of label conjugated to materials other than the indirectly labeled ligand. The method for preparing the compositions involves employing a monovalent receptor to which the label is conjugated and combining the monovalent receptor labeled conjugate to the ligand, either in pure or impure form. The mixture is then segregated according to molecular weight and the ligand conjugated to the labeled receptor isolated. This conjugate may then be directly used as a reagent in a protein binding assay, where the assay mixture is substantially free of label other than labeled receptor bound to ligand.

The labels will be for the most part of relatively low molecular weight, while the receptor is preferably a Fab fragment. The ratio of receptor to ligand will be chosen so as to provide reasonable molecular weight distinctions between unbound ligand, unbound labeled receptor, ligand bound to labeled receptor, and other materials which may be in the mixture. Various techniques may be used for the separation.

The assays are performed in accordance with known methods employing a second receptor composition, which may be labeled or unlabeled.

10 Claims, No Drawings

ASSAY EMPLOYING A LABELED FAB-FRAGMENT LIGAND COMPLEX

BACKGROUND OF THE INVENTION

1. Field of the Invention

The availability of molecules which are able to specifically bind to a particular spatial and polar organization is the basis for a wide variety of techniques referred to as competitive protein binding assays. These techniques depend upon having a member of a specific binding pair conjugated with the label which is involved with the production of a detectible signal.

Depending upon the nature of the label, various methods have evolved for distinguishing between an analyte which is bound to the corresponding member of the specific binding pair and analyte which is unbound. With the various techniques, either the receptor or the ligand is labeled. Particularly, where the receptor is labeled, the receptor is normally one component of a complex mixture of analogous composition and molecular weight. For example, antibodies which are isolated from serum will be present with globulins and other antibodies which are either non-specific or specific for a wide variety of ligands other than the ligand of interest. When labeling the receptor composition, both the receptor of interest as well as the contaminating globulins will be labeled. The label involved with extraneous receptors or other materials will act as a background in the assay, interfering with the sensitivity of the assay.

While affinity chromatography may be employed to enhance the purity of the receptor of interest, this technique has many deficiencies. One deficiency is that the most strongly binding antibodies tend to be retained by the affinity chromatography column. Secondly, there are normally substantial losses of the antibodies of interest and substantial reduction in the binding constant of the recovered antibody. It is therefore desirable to find alternative methods to provide labeled reagents having reduced amounts of label bound to extraneous materials.

2. Brief Description of the Prior Art

U.S. Pat. No. 3,998,943 discloses a fluorescent immunoassay involving a ligand conjugated to a fluorescer, employing receptor to ligand and receptor to fluorescer, where the receptor to fluorescer is inhibited from binding to fluorescer when receptor to ligand is bound to ligand. U.S. Pat. No. 3,935,074 describes an immunoassay where a receptor for a detector label and a receptor for ligand are employed with the detector label labeled to ligand. Various labels are described. U.S. Pat. No. 3,996,345 describes an assay employing a chromogenic pair, where one of the chromogens fluoresces emitting light at a wavelength within the absorption band of the other chromogen. Copending patent application Ser. No. 815,636, filed July 14, 1977 now U.S. Pat. No. 4,160,145, discloses the use of a non-enzymatic catalyst as a label in competitive protein binding assays.

Co-pending application Ser. No. 893,910, filed Apr. 5, 1978, describes a chemiluminescent label in a competitive protein binding assay. Assays dependent upon the presence of enzyme labile bonds are described in Carrico, et al, Anal. Biochem. 72, 271-282 (1976); ibid 72, 283-292 (1972).

SUMMARY OF THE INVENTION

Methods and compositions are provided for protein binding assays. The method of preparing reagents involves conjugating a relatively low molecular weight label to a monovalent receptor for a polyepitopic ligand, the ligand and receptor being members of a specific binding pair. The composition is then purified by separating the mixture according to molecular weight, so as to isolate the ligand bound to labeled receptor substantially free of other labeled compounds.

The resulting purified ligand bound to labeled monovalent receptor (labeled ligand) may then be employed as a reagent in a protein binding assay, where the presence of labeled or unlabeled polyvalent e.g. antibody, receptor bound to the labeled ligand affects the detectible signal produced by the label. Illustrative labels include fluorescers, chemiluminescers, nonenzymatic catalysts, groups having enzyme labile bonds, and the like.

Compositions are provided having labeled Fab antibodies bound to a polyepitopic ligand in the substantial absence of other labeled materials, as well as the label. These labeled ligand compositions are provided in kits with ligand receptor in premeasured amounts for use in protein binding assays.

DESCRIPTION OF THE SPECIFIC EMBODIMENTS

The subject invention is concerned with novel compositions for use in protein binding assays, methods for preparing such compositions, combinations of reagents for use in protein binding assays, and improved methods for performing protein binding assays by employing the reagents of this invention.

The reagents of this invention are prepared by conjugating a relatively low molecular weight label capable of providing a detectible signal to a monovalent receptor, where the receptor is one component of a mixture of components having analogous chemical properties. The labeled mixture, preferably segregated as to molecular weight, is then combined with a ligand which will bind solely to its reciprocal receptor. The mixture is then subjected to segregation by molecular weight, segregating and isolating those fractions involving one or more of the monovalent labeled receptor bound to ligand. The resulting product is then substantially free of other materials bound to label, as well as the label, and also unbound ligand. Since these compositions are substantially free of label which is uninvolved with the assay, as well as other interferants, the observed signal is solely derived from the label which is bound to ligand through the monovalent receptor. Thus, the background which would result from label unrelated to ligand and its reciprocal receptor is substantially diminished or absent.

The labeled receptor-ligand complex may then be employed in a protein binding assay, the technique depending upon the particular label. The complex may be provided as a reagent in a kit in combination with receptor for ligand, where the two reagents are premeasured so as to substantially optimize the sensitivity of the assay.

Definitions

Analyte—the compound or composition to be measured, which may be a polyepitopic ligand, normally antigenic, having at least two epitopic sites, a mixture of compounds which share at least two common epitopic sites, or a receptor.

Ligand—any compound for which a receptor naturally exists or can be prepared.

Receptor—any compound or composition capable of recognizing a spatial and polar organization of a molecular i.e. epitopic site. In the subject invention, there will normally be two different receptors employed. The first receptor which will be labeled, will be monovalent, having only one binding site, which binding site is specific to a particular spatial and polar organization. For the most part, the monovalent receptors will be Fab fragments of antibodies, conveniently obtained by peptidase digestion of an antibody. Since for the most part, the monovalent receptors will be Fab fragments, these receptors will normally be referred to as Fab fragments, it being understood that Fab fragments is illustrative of a broader class of monovalent receptors. The other receptors which will be employed will normally be polyvalent receptors. These receptors include antibodies, enzymes, lectins, and the like. The receptor and its reciprocal ligand form a specific or homologous binding pair. In referring to receptors to a ligand, the receptors will be referred to as "antiligand."

Label—a molecule under about 5,000 molecular weight which is capable in combination with electromagnetic radiation or auxiliary chemical reagents of producing a detectible signal, which capability is affected by the presence of labeled or unlabeled receptor bound to ligand in spatial proximity to the label. Illustrative labels include fluorescers, chemiluminescers, nonenzymatic catalysts, groups having enzymatically labile bonds, and the like.

Label-Fab—a conjugate in which the label is covalently bound to a Fab antiligand, there being on the average at least one label per Fab antiligand.

Ligand-label complex—a complex having at least one label-Fab non-covalently bound to ligand and retaining at least one free epitopic site.

Ligand-Label Complex

The ligand-label complex has three components: (1) ligand; (2) monovalent receptor (abbreviated as Fab); and (3) label. The first component to be discussed will be the ligand.

Ligand

The ligands which will be employed in the subject invention will generally have at least 15,000 molecular weight, more usually at least 25,000 molecular weight and for the most part at least 50,000 molecular weight. There is no real upper limit on molecular weight, although most compositions which will be of diagnostic interest will generally be below 2,000,000 molecular weight, more usually below 1,000,000 molecular weight. The polyepitopic ligand analytes will normally be poly(amino acids) i.e. polypeptides and proteins, polysaccharides, nucleic acids, and combinations thereof. Such combinations or assemblages include bacteria, viruses, chromosomes, genes, mitchondria, nuclei, cell membranes, and the like.

For the most part, hormones of interest will generally be from about 20,000 to 100,000 molecular weight, more usually from about 20,000 to 60,000 molecular weight. Enzymes of interest will generally range from about 20,000 to 600,000 molecular weight, more usually from 20,000 to about 300,000 molecular weight. Immunoglobulins will generally range from about 150,000 to 1,000,000 molecular weight.

The wide variety of proteins may be considered as to the family of proteins having similar structural features, proteins having particular biological functions, proteins related to specific microorganisms, particularly disease causing microorganisms, etc.

The following are classes of proteins related by structure:
protamines
histones
albumins
globulins
scleroproteins
phosphoproteins
mucoproteins
chromoproteins
lipoproteins
nucleoproteins
glycoproteins
unclassified proteins, e.g. somatotropin, prolactin, insulin, pepsin A number of proteins found in the human plasma are important clinically and include:
Prealbumin
Albumin
$\alpha_1$-Lipoprotein
$\alpha_1$-Acid glycoprotein
$\alpha_1$-Antitrypsin
$\alpha_1$-Glycoprotein
Transcortin
4.6S-Postalbumin
Tryptophan-poor $\alpha_1$-glycoprotein
$\alpha_1$X-Glycoprotein
Thyroxin-binding globulin
Inter-$\alpha$-trypsin-inhibitor
Gc-globulin
   (Gc 1-1)
   (Gc 2-1)
   (Gc 2-2)
Haptoglobin
   (Hp 1-1)
   (Hp 2-1)
   (Hp 2-2)
Ceruloplasmin
Cholinesterase
$\alpha_2$-Lipoprotein(s)
$\alpha_2$-Macroglobulin
$\alpha_2$-HS-glycoprotein
Zn-$\alpha_2$-glycoprotein
$\alpha_2$-Neuramino-glycoprotein
Erythropoietin
$\beta$-lipoprotein
Transferrin
Hemopexin
Fibrinogen
Plasminogen
$\beta_2$-glycoprotein I
$\beta_2$-glycoprotein II
Immunoglobulin G (IgG) or $\gamma$G-globulin
Mol. formula:
   $\gamma_2\kappa_2$ or $\gamma_2\lambda_2$
Immunoglobulin A (IgA) or $\gamma$A-globulin
Mol. formula:
   $(\alpha_2\kappa_2)^n$ or $(\alpha_2\lambda_2)^n$
Immunoglobulin M (IgM) or $\gamma$M-globulin
Mol. formula:
   $(\mu_2\kappa_2)^5$ or $(\mu_2\lambda_2)^5$ Immunoglobulin D(IgD) or γD-Globulin (γD)
Mol. formula:
   ($\delta_2\kappa_2$) or ($\delta_2\lambda_2$)
Immunoglobulin E (IgE) or γE-Globulin (γE)
Mol. formula:
   ($\epsilon_2\kappa_2$) or ($\epsilon_2\lambda_2$)
Free K and γ light chains
Complement factors:
C'1
  C'1q
  C'1r
  C'1s
C'2
C'3
  $\beta_1 A$
  $\alpha_2 D$
C'4
C'5
C'6
C'7
C'8
C'9
Important blood clotting factors include:

BLOOD CLOTTING FACTORS

| International designation | Name |
|---|---|
| I | Fibrinogen |
| II | Prothrombin |
| IIa | Thrombin |
| III | Tissue thromboplastin |
| V and VI | Proaccelerin, accelerator globulin |
| VII | Proconvertin |
| VIII | Antihemophilic globulin (AHG) |
| IX | Christmas factor, plasma thromboplastin component (PTC) |
| X | Stuart-Prower factor, autoprothrombin III |
| XI | Plasma thromboplastin antecedent (PTA) |
| XII | Hageman factor |
| XIII | Fibrin-stabilizing factor |

Important protein hormones include:

Peptide and Protein Hormones

Parathyroid hormone (parathromone)
Thyrocalcitonin
Insulin
Glucagon
Relaxin
Erythropoietin
Melanotropin (melanocyte-stimulating hormone; intermedin)
Somatotropin (growth hormone)
Corticotropin (adrenocorticotropic hormone)
Thyrotropin
Follicle-stimulating hormone
Luteinizing hormone (interstitial cell-stimulating hormone)
Luteomammotropic hormone (luteotropin, prolactin)
Gonadotropin (chorionic gonadotropin)

Tissue Hormones

Secretin
Gastrin
Angiotensin I and II
Bradykinin
Human placental lactogen

Peptide Hormones from the Neurohypophysis

Oxytocin
Vasopressin
Releasing factors (RF), CRF, LRF, TRF, Somatotropin-RF, GRF, FSH-RF, PIF, MIF Other polymeric materials of interest are mucopolysaccharides and polysaccharides.

Illustrative antigenic polysaccharides derived from microorganisms are as follows:

| Species of Microorganisms | Hemosensitin Found in |
|---|---|
| Streptococcus pyogenes | Polysaccharide |
| Diplococcus pneumoniae | Polysaccharide |
| Neisseria meningitidis | Polysaccharide |
| Neisseria gonorrhoeae | Polysaccharide |
| Corynebacterium diphtheriae | Polysaccharide |
| Actinobacillus mallei; Actinobacillus whitemori | Crude extract |
| Francisella tularensis | Lipopolysaccharide Polysaccharide |
| Pasteurella pestis | |
| Pasteurella pestis | Polysaccharide |
| Pasteurella multocida | Capsular antigen |
| Brucella abortus | Crude extract |
| Haemophilus influenzae | Polysaccharide |
| Haemophilus pertussis | Crude |
| Treponema reiteri | Polysaccharide |
| Veillonella | Lipopolysaccharide |
| Erysipelothrix | Polysaccharide |
| Listeria monocytogenes | Polysaccharide |
| Chromobacterium | Lipopolysaccharide |
| Mycobacterium tuberculosis | Saline extract of 90% phenol extracted mycobacteria and polysaccharide fraction of cells and tuberculin |
| Klebsiella aerogenes | Polysaccharide |
| Klebsiella cloacae | Polysaccharide |
| Salmonella typhosa | Lipopolysaccharide, Polysaccharide |
| Salmonella typhi-murium; Salmonella derby Salmonella pullorum | Polysaccharide |
| Shigella dysenteriae | Polysaccharide |
| Shigella flexneri | |
| Shigella sonnei | Crude, polysaccharide |
| Rickettsiae | Crude extract |
| Candida albicans | Polysaccharide |
| Entamoeba histolytica | Crude extract |

The microorganisms which are assayed may be intact, lysed, ground or otherwise fragmented, and the resulting composition or portion, e.g. by extraction, assayed. Microorganisms of interest include:

Corynebacteria

*Corynebacterium diptheriae*

Pneumococci

*Diplococcus pneumoniae*

Streptococci

*Streptococcus pyogenes*
Streptococcus salivarus

Staphylococci

*Staphylococcus aureus*
Staphylococcus albus

Neisseriae

*Neisseria meningitidis*
Neisseria gonorrheae

| Enterobacteriaciae | |
|---|---|
| *Escherichia coli* | |
| *Aerobacter aerogenes* | } The coliform bacteria |
| *Klebsiella pneumoniae* | |
| *Salmonella typhosa* | |
| *Salmonella choleraesuis* | } The Salmonellae |
| *Salmonella typhimurium* | |
| *Shigella dysenteriae* | |
| *Shigella schmitzii* | |
| *Shigella arabinotarda* | } The Shigellae |
| *Shigella flexneri* | |
| *Shigella boydii* | |
| *Shigella Sonnei* | |
| Other enteric bacilli | |
| *Proteus vulgaris* | |
| *Proteus mirabilis* | } Proteus species |
| *Proteus morgani* | |
| *Pseudomonas aeruginosa* | |
| *Alcaligenes faecalis* | |
| *Vibrio cholerae* | |

Hemophilus-Bordetella group

*Hemophilus influenzae,*
   *H. ducreyi*
   *H. hemophilus*
   *H. aegypticus*
   *H. paraiufluenzae*
*Bordetella pertussis*

Pasteurellae

*Pasteurella pestis*
*Pasteurella tulareusis*

Brucellae

*Brucella melitensis*
*Brucella abortus*
*Brucella suis*

Aerobic Spore-forming Bacilli

*Bacillus anthracis*
*Bacillus subtilis*
*Bacillus megaterium*
*Bacillus cereus*

Anaerobic Spore-forming Bacilli

*Clostridium botulinum*
*Clostridium tetani*
*Clostridium perfringens*
*Clostridium novyi*
*Clostridium septicum*
*Clostridium histolyticum*
*Clostridium tertium*
*Clostridium bifermentans*
*Clostridium sporogenes*

Mycobacteria

*Mycobacterium tuberculosis hominis*
*Mycobacterium bovis*
*Mycobacterium avium*
Mycobacterium leprae
Mycobacterium paratuberculosis

Actinomycetes (fungus-like bacteria)

*Actinomyces israelii*
*Actinomyces bovis*
*Actinomyces naeslundii*
*Nocardia asteroides*
*Nocardia brasiliensis*

The Spirochetes

*Treponema pallidum*
*Treponema pertenue*
*Treponema carateum*
*Borrelia recurrentis*
*Leptospira icterohemorrhagiae*
*Leptospira canicola*
*Spirillum minus*
*Streptobacillus moniliformis*

Mycoplasmas

*Mycoplasma pneumoniae*

Other pathogens

*Listeria monocytogenes*
*Erysipelothrix rhusiopathiae*
*Streptobacillus moniliformis*
*Donvania granulomatis*
*Bartonella bacilliformis*

Rickettsiae (bacteria-like parasites)

*Rickettsia prowazekii*
*Rickettsia mooseri*
*Rickettsia rickettsii*
*Rickettsia conori*
*Rickettsia australis*
*Rickettsia sibiricus*
Rickettsia akari
*Rickettsia tsutsugamushi*
*Rickettsia burnetii*
*Rickettsia quintana*

Chlamydia (unclassifiable parasites bacterial/viral)

Chlamydia agents (naming uncertain)

| Fungi |
|---|
| *Cryptococcus neoformans* |
| *Blastomyces dermatidis* |
| *Histoplasma capsulatum* |
| *Coccidioides immitis* |
| *Paracoccidiodes brasiliensis* |
| *Candida albicans* |
| *Aspergillus fumigatus* |
| *Mucor corymbifer* (*Absidia corymbifera*) |
| *Rhizopus oryzae*         } |
| *Rhizopus arrhizus*     } Phycomycetes |
| *Rhizopus nigricans*    } |
| *Sporotrichum schenkii* |
| *Fonsecaea pedrosoi* |
| *Fonsecaea compacta* |
| *Fonsecaea dermatitidis* |
| *Cladosporium carrionii* |
| *Phialophora verrucosa* |
| *Aspergillus nidulans* |
| *Madurella mycetomi* |
| *Madurella grisea* |
| *Allescheria boydii* |
| *Phialosphora jeanselmei* |
| *Microsporum gypseum* |
| *Trichophyton mentagrophytes* |
| *Keratinomyces ajelloi* |
| *Microsporum canis* |
| *Trichophyton rubrum* |
| *Microsporum andouini* |

Viruses

Adenoviruses

Herpes viruses

Herpes simplex
Varicella (Chicken pox)
Herpes Zoster (Shingles)
Virus B
Cytomegalovirus

Pox Viruses

Variola (smallpox)
Vaccinia
*Poxvirus bovis*
Paravaccinia
*Molluscum contagiosum*

Picornaviruses

Poliovirus
Coxsackievirus
Echoviruses
Rhinoviruses

Myxoviruses

Influenza (A, B, and C)
Parainfluenza (1-4)
Mumps Virus
Newcastle Disease Virus
Measles Virus
Rinderpest Virus
Canine Distemper Virus
Respiratory Syncytial Virus
Rubella Virus

Arboviruses

Eastern Equine Eucephalitis Virus
Western Equine Eucephalitis Virus
Sindbis Virus
Chikugunya Virus
Semliki Forest Virus
Mayora Virus
St. Louis Encephalitis Virus
California Encephalitis Virus
Colorado Tick Fever Virus
Yellow Fever Virus
Dengue Virus

Reoviruses

Reovirus Types 1-3

Hepatitis

Hepatitis A Virus
Hepatitis B Virus

Tumor Viruses

Rauscher Leukemia Virus
Gross Virus
Maloney Leukemia Virus

Allergens

Receptor

The next component is the monovalent receptor. While there will be some naturally occurring monovalent receptors, for the most part, the monovalent receptors will be Fab fragments of antibodies. Fab fragments are well known and a description may be found in Advanced Immunochemistry, Eugene Day. The Williams & Wilkins Company, Baltimore, 1972, pp. 88ff. Fab fragments can be produced by digestion with a peptidase, such as papain, trypsin, or pepsin. Other treatments may be involved such as reduction, substitution, e.g. aminoethylation, carboxyalkylation with, for example, iodoacetamide, and the like. The fragment will normally have about 40,000 molecular weight, be monovalent and retain a high degree of the specificity and binding constant of the intact antibody.

Label

The label is characterized by being a small molecule, generally below about 2,000 molecular weight, more usually below about 1,000 molecular weight, greater than about 100 molecular weight and preferably from about 125 to about 800 molecular weight.

The label is further characterized by having either a chemical or physical (electronic) transformation affected by the spatial proximity of the receptor or a label on the receptor. The effect of the spatial proximity of the receptor may be one of steric bulk impeding the approach of a large molecule to the label or a change of environment in the area of the label. Alternatively, the receptor may be labeled with a companion label, which interacts with the label of the complex when in close proximity, so as to modify the signal from the label of the complex.

While the label can be involved in a single event, desirably, the label will be capable of producing a plurality of events, so that a multiplication of the effect may be achieved.

The labels will be for the most part simple organic molecules which either absorb electromagnetic radiation or produce a product which will absorb electromagnetic radiation.

The first class of compounds of interest are fluorescers. These compounds will for the most part absorb light above 300 nm, preferably above 350 nm and more preferably above 400 nm. These compounds will preferably have extinction coefficients of at least $10^3$, preferably at least $10^4$ above the indicated wavelengths.

Various chromophores which may be employed as fluorescers include the xanthene dyes, which include the fluoresceins derived from 3,6-dihydroxy-9-phenylxanthhydrol and rosamines and rhodamines, derived from 3,6-diamino-9-phenylxanthhydrol. The rhodamines and fluoresceins have a 9-o-carboxyphenyl group and are derivatives of 9-o-carboxyphenylxanthhydrol.

These compounds are commercially available with substituents on the phenyl group which can be used as the site for bonding or as the bonding functionality. For example, amino and isothiocyanate substituted fluorescein compounds are available.

Other dyes which may be used as fluorescers include 3-phenyl-7-isocyanatocoumarin, acridines, such as 9-isothiocyanatoacridine and acridine orange N-(p-(2-benzoxazolyl)phenyl)maleimide; benzoxadiazoles, such as 4-chloro-7-nitrobenzo-2-oxa-1,3-diazole and 7-(p-methoxybenzylamino)-4-nitrobenzo-2-oxa-1,3-diazole; stilbenes, such as 4-dimethylamino-4'-isothiocyanatostilbene and 4-dimethylamino-4'-maleimidostilbene N,N'-dioctadecyl oxacarbocyanine p-toluenesulfonate; pyrenes, such as 8-hydroxy-1,3,6-pyrenetrisulfonic acid, and 1-pyrenebutyric acid; merocyanines e.g. merocyanine 540; rose bengal; 2,4-diphenyl-3(2H)-furanone; cyanines; anthraquinones; porphyrins; triarylmethanes; as well as other readily available dyes which are capable of fluorescing. These dyes, either have active functionalities for conjugation or such functionalities may be readily introduced.

It should further be noted that the absorption and emission characteristics of the dye may vary from being free in solution and being bound to a protein or ligand. Therefore, when referring to the various wavelength ranges and characteristics of the dyes, it is intended to indicate the dyes as employed and not the dye which is unconjugated and characteristized in an arbitrary solvent.

The next type of label is a chemiluminescent compound, which by reacting with a compound in solution is capable of producing light. Therefore, a chemiluminescent source will normally have at least two components.

For purposes of convenience, the chemiluminescent source will be divided into two categories: those which do not involve the intermediacy of enzyme catalysis; and those which do involve enzyme catalysis.

Considering chemiluminescent sources which do not involve enzyme catalysis, only those sources can be employed which chemiluminesce under conditions which neither inhibit the binding of the receptor to the ligand, nor degrade the receptor and ligand at an unacceptable rate during the period of measurement. While ordinarily chemiluminescent sources which are dependent upon nonaqueous solvents and strong basic conditions, greater than pH11, will not be useful, techniques can be employed involving rapid injection or flow techniques where the modulated emission is substantially completed before the protein is denatured and significant dissociation occurs. After injection of base, one would observe a burst of light which could be measured.

A diverse number of families of compounds have been found to provide chemiluminescence under a variety of conditions. One family of compounds is 2,3-dihydro-1,4-phthalazinediones. The most popular compound is luminol, which is the 5-amino compound. Other members of the family include the 5-amino-6,7,8-trimethoxy and the dimethylamino[ca]benz analog. These compounds can be made to luminesce with alkaline hydrogen peroxide or calcium hypochlorite and base. Another family of compounds is the 2,4,5-triphenylimidazoles, with lophine as the common name for the parent product. Chemiluminescent analogs include para-dimethylamino and -methoxy substituents.

The next group of chemiluminescent compounds are indolen-3-yl hydroperoxides, precursors thereto and derivatives thereof.

The next group of compounds are the bis-9,9'-biacridinium salts, of which lucigenin, N,N'-dimethyl-9,9'-biacridinium dinitrate is illustrative. These compounds chemiluminesce upon combination with alkaline hydrogen peroxide.

The next group of compounds are acridinium salts which are substituted in the 9 position. Particular substituents are carboxylic esters, particularly the aryl esters, acyl substituents, particularly benzoyl, and cyano. Alkaline hydrogen peroxide is employed to induce chemiluminescence.

Another group of compounds are various acyl peroxy esters and hydroperoxides, which may be formed in situ in combination with compounds such as 9,10-diphenylanthracene.

Another source of chemiluminescence is hydroperoxides e.g. tetralin hydroperoxide in combination with metal complexes, particularly porphyrins and phthalocyanines, where the metals are iron and zinc.

Preferred systems are those which provide a satisfactory quantum efficiency of emission from the chemiluminescer at a pH at or below 11, preferably at or below 10.

The next group of compounds are based on chemiluminescers which chemiluminesce under enzymatic catalysis. Primarily, there are two groups of enzymatically catalyzed chemiluminescers. The first group are those compounds which chemiluminesce in combination with alkaline hydrogen peroxide. By employing a peroxidase e.g. horseradish peroxidase, in combination with hydrogen peroxide and the chemiluminescer, chemiluminescence can be achieved. Illustrative systems include 2,3-dihydro-1,4-phthalazinediones.

The second enzymatic source of chemiluminescence is based on luciferins and their analogs and luciferases.

The next group of compounds concerns non-enzymatic catalysis. These catalysts are involved with electron transfer agents. One agent acts by the transferring of two electrons ($R^2$), the second electron transfer agent acts by the transferring of one electron ($R^1$) and an intermediate or catalyst agent serves as the label and is able to receive and transfer one and two electrons. In some instances, the intermediate or catalyst may react as either $R^1$ or $R^2$, where the particular catalyst cannot react with a particular electron transfer reagent or family of reagents.

The label will for the most part be either metal complexes or aromatic compounds capable of assuming a neutral or changed quinone structure with a heteroatom of atomic number 7 to 8 i.e. oxygen and nitrogen. For the most part, the label will be aromatic having from one to five, usually one to four, fused or non-fused rings, where one or more heteroatoms may be involved as annular atoms. The labels will be able to assume either an o-quinone or p-quinone structure, either outside of or as part of a cyclic structure. Therefore, common to the label which does not involve a metal will be the following formulii.

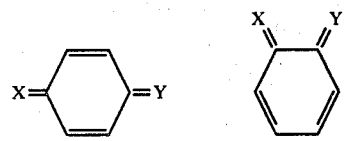

where X and Y can be the same or different and X is oxygen or nitrogen and Y is oxygen, nitrogen or carbon, and wherein X and Y, as well as the annular atoms may be further substituted.

The first group of compounds are the quinones, either ortho or para, where the heteroatoms are not involved in a heterocyclic structure. These compounds will for the most part have the following formulii.

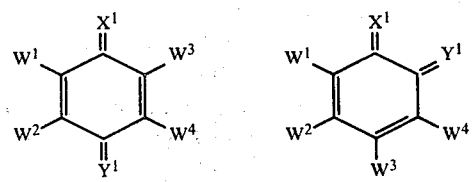

wherein $X^1$ and $Y^1$ are oxygen or imino, more usually oxygen;

$W^{1-4}$ may be hydrogen, halogen, particularly of atomic number 9 to 35, more particularly of atomic number 17 to 35, alkyl of from 1 to 6 carbon atoms, more usually of from 1 to 4 carbon atoms or W groups on adjacent carbon atoms, particularly $W^1$ and $W^2$ or $W^3$ and $W^4$, may be taken together to form an aromatic ring, particularly a benzene ring, either substituted or unsubstituted, normally having not more than about 2 substituents which are alkyl or heteroatom or atomic numbers 7 to 8. which include hydroxy, alkoxy, amino having from 0 to 2 alkyl groups, e.g. alkylamino, and dialkylamino, wherein the alkyl groups are of from 1 to 6, more usually of from 1 to 3 carbon atoms.

Generally, the quinones will have from 1 to 3 rings, usually fused rings, and will be of from about 6 to 20 carbon atoms, more usually of from about 6 to 16 carbon atoms. The total number of heteroatoms will generally be in the range of from about 2 to 8, more usually from 2 to 6.

Illustrative quinones include alizarin, 1,2-naphthoquinone, chloranil, 2,6-dichlorophenolindophenol and 2,6-dibromophenolindophenol.

The next group of compounds are those which are basically internal o-quinonediimines. These compounds for the most part will have the following formulii.

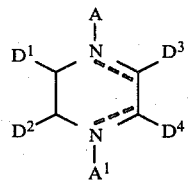

wherein:
the broken lines indicate the presence or absence of a double bond, the double bonds normally being present in the oxidized form, usually not more than one of the double bonds being present in the reduced form;

A and $A^1$ may be the same or different and may be an unshared pair of electrons, hydrogen, alkyl of from 1 to 6 carbon atoms, hydroxyalkyl of from 5 to 6 carbon atoms, particularly sugars e.g. ribityl, A and $A^1$ normally being other than hydrogen when the broken line forms a double bond, and usually one of A and $A^1$ is other than hydrogen or an unshared pair of electrons;

$D^{1-4}$ may be the same or different and are hydrogen, halo, particularly chloro, oxy e.g. alkoxy of from 1 to 6, usually 1 to 3 carbon atoms, or amino having from 0 to 2 alkyl groups of from 1 to 6, usually 1 to 3 carbon atoms; or each of the pairs of $D^1$ and $D^2$ and $D^3$ and $D^4$ may be taken together to form six membered rings, which with the atoms to which they are attached will be substituted (see the above substituents) or unsubstituted carbocyclic or heterocyclic aromatic rings having six annular members, having from 0 to 2 nitrogen annular members and having from 0 to 4, usually 2 to 4 substituents on the rings which may be alkyl of from one to six carbon atoms, more usually of from one to four carbon atoms, oxy, which is hydroxy or alkoxy, or amino, alkylamino or dialkylamino (0 to 2 alkyl groups) wherein the alkyl groups are of from 1 to 6, more usually of from 1 to 3 carbon atoms e.g. methyl.

Instances where a cyclic lactam is involved, will be treated in this invention as their enol form.

The compounds will be of from 5 to 20 carbon atoms, more usually of from 12 to 18 carbon atoms and having 2 to 8 heteroatoms, more usually 2 to 6 heteroatoms, and preferably 4 to 6 heteroatoms which are oxygen and nitrogen.

Where positive nitrogen is involved, there will normally be an anionic counterion, which may be any anion in solution, usually being halo e.g. chloro and bromo, sulfate, phosphate or borate.

Illustrative compounds include flavins, e.g. flavin, riboflavin, galactoflavin, and lumiflavin, pyocyanine, neutral red, safranine and phenazine methosulfate.

The next group of compounds are biaryls which will have the following formula wherein:

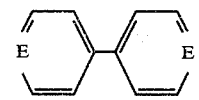

E is carbon substituted nitrogen, wherein the substituents are alkyl of from 1 to 10, usually of from 1 to 8 carbon atoms, or aminocarbon e.g. $C-NJ_2$, wherein the carbon is an annular member and the amino group has from 0 to 2 alkyl substituents (J), usually 2 alkyl substituents of from 1 to 6 carbon atoms, more usually of from 1 to 3 carbon atoms.

The compounds will normally have from 12 to 30 carbon atoms, more usually from 12 to 26 carbon atoms, generally having from 2 to 4 heteroatoms which are nitrogen and oxygen, particularly nitrogen.

Illustrative compounds include methylviologen benzylviologen, and Wurster's blue.

The next group of compounds are heterocyclics having one nitrogen and a second heteroannular member which is chalcogen (oxygen or sulfur). These compounds will for the most part have the following formula. 5.

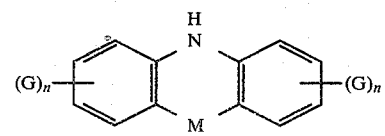

wherein
M is chalcogen (oxygen or sulfur), G is alkyl, oxy, which includes hydroxy or alkoxy, or amino, which includes alkylamino and dialkylamino, wherein the alkyl groups are of from 1 to 6, usually of from 1 to 3 carbon atoms, or adjacent Gs may be taken together to form a fused benzene ring with the annular carbon atoms to which they are attached; and
n is of from 0 to 2, usually of from 1 to 2.

The total number of heteroatoms will normally be of from 2 to 6, more usually of from 4 to 6, and the total number of carbon atoms will normally be of from 12 to 20, more usually of from 12 to 16. Illustrative compounds include brilliant cresyl blue, methylene blue and Meldola Blue.

In each instance, the compound will be functionalized to provide for a linking group for binding to the ligand. As indicated previously, the linking group for bonding ligand analog to the hub nucleus can also be employed for linking the label to the ligand. In effect, a hydrogen atom of the label will be substituted with a functionality which provides for covalent bonding to the ligand.

A wide variety of complex metal compounds can be employed as the label. Illustrative of metals are cobalt and iron, which may be complexed with porphyrins, phthalocyanines, phenanthrolines or other covenient complexing agents.

metmyoglobin, pentacyanonitrosoferrate, naphthoquinones, nitroxides, nitramine, metal complexes, such as cobalt, iron, molybdenum and vanadium, metallocenes, particularly of titanium and vanadium, methylene blue, viologens and tetrazolium salts.

The following table provides various pairs of electron transfer reagents and an appropriate label. For each of the references, the various reactants and catalysts which were tested are reported. Frequently, a number of different combinations were employed.

TABLE I

| Reference | Electron Transfer Agent, $R^2$ | Label | Electron Transfer Agent, $R^1$ |
|---|---|---|---|
| 1 | NADH derivatives | FMN | $O_2$ |
| 2 | NADH | FMN | Methemoglobin |
|  |  | FAD | Metmyoglobin |
|  |  | Methylene Blue |  |
| 3 | NADH | FMN | $Na_2FeCN_5NO$ |
| 4,5,6 | N-benzyl 1,2-dihydronicotinamide (I) | Riboflavin | $O_2$ |
|  |  | Neutral Red | 2,2,6,6-tetramethyl-piperidone-4-oxyl-1 |
|  | 2,6-dimethyl-3,5-dicarboethoxy-1,4-dihydropyridine (II) | FMN |  |
|  |  | Galactoflavin |  |
|  | bis-2,2'-di(N-benzyl dihydronicotinamide) | Methylene blue | p-NOdimethylaniline |
|  |  | 4,6-di-(tert-butyl)-o-benzoquinone | nitramine |
|  |  | 1,2-naphthoquinone | $CO^{+3}$, $Fe^{+3}$, Mo and Va acetylacetonate |
|  |  | alizarin | Biscyclopentadienylt-tanium dichloride |
|  |  | dibromophenol indophenol |  |
|  |  | dichlorophenol indophenol | Biscyclopentadienylv-adium dichloride |
| 4 | $Na_2S_2O_4$ | N-propyl 1,4-dihydro-nicotinamide | 2,4,6-tri(tert-but phenoxyl radical |
| 7 | Thiol(mercaptoethanol) | Vitamin $B_{12}$ | Methylene Blue |
|  | NaSH | iron porphyrin | Nile Blue A |
|  | ascorbic acid | Factor B | Safranine T |
|  | reductone | Cyanocobalamin | Janus green |
|  | phenylhydrazine | Hemin | benzyl viologen |
|  | hydrazine | meso-tetra(p-carboxyphenyl)-porphino cobalt | methyl viologen |
|  |  | Co phthalocyanine |  |
| 8 | II | phenazinemethosulfate | methyl viologen |
|  |  | pyocyanine | triphenyltetrazolium |
|  |  |  | anthraquinone |
|  |  |  | acenaphthenequinone |
| 9 | I | Wurster's Blue | $O_2$ |
| 10 | I | 2,6-diiodo-4-aminophenol | $O_2$ |
|  | pyronine(H) | Meldola Blue | iron complex |
|  | NADH | Meldola Blue | triphenyltetrazolium |

[1]Wu et al, Biochemistry 9, 2219 (1970)
[2]Brown & Synder, J. Biol. Chem. 244, 6702 (1969)
[3]Fox & Tollin, Biochemistry 5, 3873 (1960)
[4]Mozzhukin et al, Zhur. Obsh. Khim. 37, 1494 (1967)
[5]Aleksandrova et al, Dokl. Akad. Nauk. SSR 167, 1291 (1966)
[6]Zelenin et al, Zhur. Obsh. Khim. 37,1500 (1967)
[7]Schrauzer & Sibent, Arch. Biochem. Biophys. 130, 257 (1969)
[8]Kito et al, Chemistry Letters 1974, 353
[9]Bechara & Cilento, Biochemistry 11, 2606 (1972)
[10]Cilento & Arauyo, Chem. Comm. 1968, 1420

The electron transfer agents may be varied widely and will depend upon the label employed as well as the correlative electron transfer agent. Included among electron transfer agents are dihydropyridines illustrated by 1-benzyl-1,4-dihydroicotinamide, NADH, and Hanztsch ester (having alkyl esters of from 1 to 6 carbon atoms), thiols, ascorbic acid, reductone, phenylhydrazine, hydrazine, Nile Blue A, Safranine T, Phensafranine, Janus Green and viologens. These compounds will normally be employed as electron sources, providing for two electron transfers.

A wide variety of compounds can be employed as electron recipients, normally receiving one electron. These compounds include oxygen, methemoglobin, For the most part, the electron transfer reagents will be small molecules, generally of molecular weight in the range of about 34 to 1,000, usually in the range of about 100 to 800. In order to enhance the steric inhibition by the receptor of the approach of one or both of the redox reactants, one or both of the redox reactants may be covalently or non-covalently bound to a macromolecular water soluble molecule.

The next group of labels are those which involve compounds capable of reacting as an enzyme substrate, particularly compounds involving a coenzyme or light emitter. The reactions involved will normally be oxidative, reductive or cleavage e.g. hydrolysis.

For the most part, the compounds undergoing oxidation and/or reduction will be coenzymes or mimetic analogs thereof. Illustrative coenzymes include nicotinamide adenine dinucleotide, its phosphate, and the reduced forms thereof, flavins, which includes flavin mononucleotide, flavine adenine dinucleotide, riboflavin, flavoquinone, lumiflavin, and the analogs thereof, cytochromes e.g. cytochrome C, cobalamins and cobamides e.g. vitamin $B_{12}$.

Enzymes which employ NAD or NADH or their phosphates include particularly the NAD dependent dehydrodgenases e.g. malate dehydrogenase, glucose-6-phosphate dehydrogenase, lactate dehydrogenase, glyceraldehyde-3-phosphate dehydrogenase, alcohol dehydrogenase, glycerol dehydrogenase, hydroxysteroid dehydrogenase and diaphorase.

Enzymes which employ the flavins include bacterial luciferase, amino acid oxidase, dihydroorotate dehydrogenase, xanthine dehydrogenase, lipoamide dehydrogenase, NADPH-cytochrome reductase, α-glycerophosphate dehydrogenase, succinate dehyrogenase, and NADH dehydrogenase.

Enzymes which employ cobalamins or cobalamides include ribonucleotide reductase, dioldehydrase and glycerol dehydrase.

A much broader spectrum of labels is available by employing hydrolases. With hydrolases, which includes esterases, phosphatases, and sulfatases, one can provide for cleavage of a group from the complex which can then be measured either directly or indirectly or cleavage of a group which allows for retention of a molecule in the complex, which is activated or can be activated to provide a detectable signal.

All of the aforementioned labels can be used in this manner, either being released from the complex or being activated by removal of a group which inactivates the label. Because of the wide diversity of possibilities, only a few illustrations will be provided.

The first illustration will involve groups which are retained in the complex, but are activated by removal of a deactivating group by cleavage of a bond. Luminescers, fluorescers and chemiluminescers, frequently have hydroxyl groups to which phosphate or a glycosidyl group may be attached. Upon removal of the protective group, the luminescer is then capable of luminescence. Illustrative compounds include the xanthene dyes 2,3-dihydro-1,4-phthalazinediones, umbelliferone, β-naphthol, 3-pyridol, and resorufin.

Rather than having the label remain bound to the complex, an enzymatically labile bond can be provided which can be cleaved to release the label to allow it to undergo further reaction. Particularly useful are enzyme substrates, particularly coenzymes, which can be cycled, so that the cleavage of a single label will result in a plurality of detectable events.

The following table illustrates a number of exemplary systems.

TABLE II

Label - NAD or NADP ethanol $\xrightarrow{\text{alcohol dehydrogenase}}$ acetaldehyde

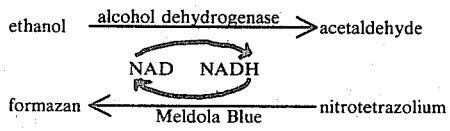

formazan $\xleftarrow{\text{Meldola Blue}}$ nitrotetrazolium

TABLE II-continued

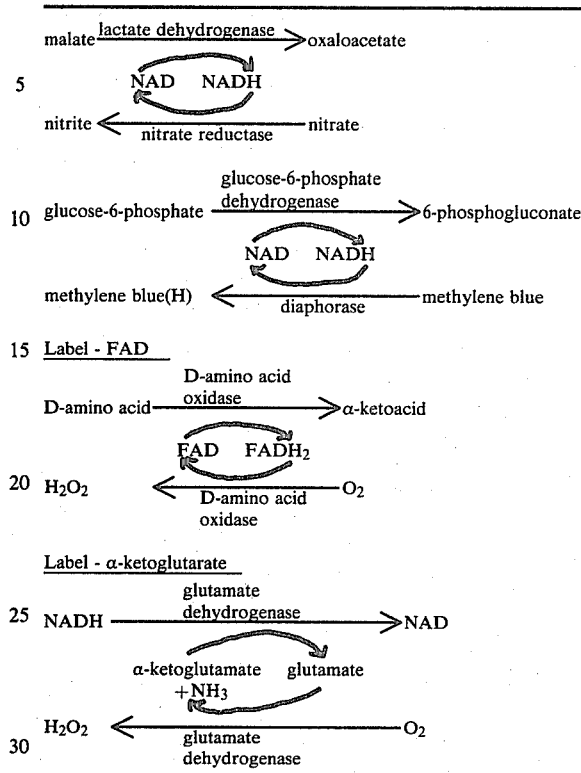

The number of labels per Fab will vary depending upon the nature of the label, the desired sensitivity of the assay, the affect of the label on the physical and chemical properties of the Fab and the like. Usually, on the average, there will be at least one label per Fab and not more than 20, usually not more than 12, and generally in the range of about 2 to 10.

Preparation of Labeled Fab

The conjugation of the label to the Fab will vary depending upon the type of label. With many labels, e.g. fluorescers, the label is commercially available with an active group for conjugation to proteins. For the most part, the active group which will be used will involve a non-oxo carbonyl (including its nitrogen and sulfur analogs) as illustrated by carboxylic acids activated with carbodiimide, carbonate monoester as a mixed anhydride, carbonyl chloride, active ester e.g. N-hydroxy succinimide, and p-nitrophenyl, isocyanate, isothiocyanate, imidate ester, thioester, thionoester, thiothionoester, and the like. Reductive alkylation employing an aldehyde and a reductant e.g. borohydride may be employed. Active halogen may be used, such as bromoacetyl groups. Alternatively, two groups can be used, such as a combination of active halogen and a mercaptan or maleimide and a mercaptan.

The reactions for the most part are carried out in aqueous solvents having up to about 40 volume percent of an inert polar organic solvent at moderate temperatures, $-10°$ to $50°$ C., and normally at pHs in the range of about 5 to 10. For the most part, the techniques described above have appeared in the literature.

Desirably, the Fab composition, either prior to or subsequent to labeling, usually prior to labeling, will be purified according to molecular weight, particularly to remove other receptor material. Purification by molecular weight differentiation or fractionation can employ any conventional process, such as chromatography, electrophores is ultracentrifugation, or the like.

Preparation of the ligand-label complex

The ligand-label complex is prepared in an aqueous medium, at mild pH, generally close to the optimum pH for binding, 5.5–9.5, usually 7 to 8.5, of the label-Fab and the ligand. Generally, an approximately equimolar amount of the two members of the complex will be added to provide the desired average label/ligand mole ratio. It is essential that the complex retain at least one free ligand epitopic site. The concentrations of the two complex members will generally be in the range of about 0.001 to 2, usually 0.01 to 1 mg/ml.

Other materials may also be included such as neutral salts e.g. sodium chloride, buffers, such as phosphate, borate, tris, etc., as well as preservatives stabilizers, and the like. For the most part, the concentrations will vary from about $10^{-4}$ to 1 M.

After the members of the complex are combined, the mixture is incubated at a mild temperature, usually in the range of about 10° to 50° C., preferably 15° to 30° C. for a moderate length of time 0.1 to 2 hours, there normally being no advantage in further extending the incubation period.

The product is then isolated by molecular weight separation, employing gel chromatography, ultracentrifugation, electrophoresis, and the like.

Usually, there will be on the average at least one Fab per ligand and not more than one Fab per 15,000 molecular weight usually not more than one Fab per 25,000 molecular weight of ligand.

The Fab is obtained from a serum protein derived composition, where antiligand is subjected to peptidase degradation and may then be subjected to sulfhydryl substitution to cap the sulfhydryl groups. The Fab is then isolated according to conventional means and conjugated with the label as previously described.

Assays

For the most part, the assays will be carried out in conventional manners. The primary difference between the assays in the literature and the subject assay is the employment of the complex as a labeled ligand, where the label is not covalently bound to the ligand, but rather bound through the intermediacy of the Fab antiligand. Since the assays have been described in the literature, and since a wide variety of labels can be used which change the nature of the assay to varying degrees, only generalizations will be made concerning the assays. The assays in which the subject invention find use are predicated on the effect resulting from the proximity of recepor to label, either due to the steric bulk of the receptor or to a group conjugated to the receptor which interacts with the label e.g. quencher conjugated to receptor which interacts with a fluorescent label.

The analyte can be either the ligand or the receptor. Where the assay method does not require labeled receptor as a reagent for ligand, no receptor will be required as a reagent when the analyte is receptor. When ligand is the analtye, then additional receptor will be required. Where labeled receptor is employed, labeled receptor will always be employed, regardless of whether the analyte is ligand or receptor.

The order of addition of reagents is not critical, although it will generally be undesirable to combine the complex (labeled Fab-ligand) with receptor prior to the addition of analyte. Either the analyte and receptor may be combined initially, followed by the addition of the complex, or the three may be combined substantially simultaneously. The order of addition will depend to some degree on the rate of dissociation of the ligand and antiligand.

Normally, aqueous solutions will be employed for the assay having up to about 40% of an inert polar organic solvent, e.g. ethers, alcohols, and the like. The pH of the medium will generally be in the range of about 5 to 10, more usually in the range of about 6 to 9. Various conventional buffers may be employed, such as carbonate, phosphate, Tris, borate, etc. Other auxiliary materials may be included, such as proteins, stabilizers, surfactants, and the like.

Where the label is a fluorescer, the receptor will normally be labeled with a quencher molecule, which is a chromophore which absorbs light in the wavelength range emitted by the fluorescer. See U.S. Pat. No. 3,996,345 for a description of the method in detail. The method employing a nonenzymatic catalysis is described in detail in co-pending application Ser. No. 815,636, filed July 14, 1977. The technique employing enzyme labile bonds is described in German Offenlegungschriften Nos. 2,618,419 and 2,618,511.

The steric bulk of the antiligand can act to prevent the approach of a large molecule, such as a receptor e.g. antibody or enzyme, from approaching the label. Where the label is a fluorescer, antifluorescer can be inhibited from binding to the fluorescer, where binding has the effect of quenching the fluorescence. Antichemiluminescer can be employed to inhibit chemiluminescence. For enzyme labile bonds, enzymes can be inhibited from binding to the bond or group with which the enzymes binds.

Depending on the particular technique, the absorption or emission of light will be determined and related to values obtained with samples having known amounts of ligand.

The following examples are offered by way of illustration and not by way of limitation.

EXPERIMENTAL

All temperatures not otherwise indicated are in centigrade. Parts and percents are by weight except where mixtures of liquids are employed and are then by volume. The following abbreviations are employed: RT-room temperature; EDTA-ethylenediaminetetraacetic acid; PBS-phosphate buffered saline; PEG-polyethylene glycol; FITC-fluoresceinisothiocyanate; TRITC-tetramethylrhodamineisothiocyanate. All fluorescence measurements were done on the Perkin-Elmer No. 1000 equipped with interference filters from Baird-Atomic: E-5 for excitation (491 nm) and No. 81-33-87 (520 nm) for emission.

EXAMPLE 1

Preparation of Fab(anti(hIgG)) (hIgG=human immunoglobulin G) and labeling with Fluorescein A sample (50 ml) of sheep serum containing anti(-hIgG) was precipitated with 50 ml of saturated ammonium sulfate. The precipitate was centrifuge (20 min at 48,200× g) and resuspended in PBS (0.04 M phosphate in saline pH 7.2). The suspension was dialyzed against the same buffer for 2 days, the final concentration being 90.8 mg/ml.

A 4.41 ml aliquot of the above protein solution in PBS (400 mg protein) was combined with 2 ml of PBS containing 0.05 M cysteine and 0.02 M EDTA, 13.59 ml PBS and 4 mg papain (Sigma, 0.16 ml of a 25 mg/ml suspension). The substrate solution had been warmed to 37° before the enzyme addition and the mixture was allowed to incubate overnight with stirring at 37°. After adjusting the pH to 6.5 with 1 N HCl, 2.2 ml of a 0.055 M iodoacetamide solution was added, the mixture incubated for 5 min at RT and dialysis initiated against 0.01 M phosphate, pH 6.5. A slight precipitation which formed was removed by centrifugation and the clear solution dialzyed against 0.15 M NaCl.

After dialysis, the material was made 0.05 m in zinc sulfate by the addition of 0.25 M zinc sulfate and allowed to sit at RM for 2 hrs. The resulting precipitate was centifuged (20 min at 48,200× g) and sodium EDTA added slowly as a solid with stirring to provide a 1% solution. The resulting precipitate was removed by centrifugation and the solution then dialyzed against PBS. The final product contained 147 mg of protein.

The Fab prepared above was labeled with FITC, following the procedure described in Example 2 to provide a F/P ratio of about 7 mole/mole.

EXAMPLE 2

Conjugation of Fab (anti(hIgG)) with FITC (FFab(hIgG))

To 4 ml of a Fab (anti(hIgG)) solution adjusted to pH 8.75 with potassium monoacid phosphate ($K_2HPO_4$) was added 1.4 mg of FITC and the mixture allowed to stand for 2 hrs at RT. The mixture was separated on Sephadex G-25 (0.9×15 cm) equilibrated with 0.05 M phosphate, pH 8 (0.05% sodium azide). The arly fraction was collected which had the characteristic yellow color. The concentration of protein in the eluent was estimated from the absorption spectrum as 2.8 mg/ml.

EXAMPLE 3

Separation of Fab-hIgG complexes ($(FFab)_n (hIgG)_m$) on Sephadex

A plurality of preparations were made by adding 0.5 ml of the above prepared fluorescein labeled Fab with differing amounts of hIgG (from Miles Laboratories). After stirring for 0.5 hr at RT, the mixture was separated on Sephadex G-200 (1.5×40 cm) equilibrated with 0.01 M PBS, pH 7.4 with a flow rate of 1 drop/40 sec and collecting 20 drops per tube. Fractions collected were further characterized by uv spectra and the Fab/hIgG ratio calculated according to the following equation.

$$\text{Fab/IgG mole/mole} = \frac{3F/P}{F/P_{FAB} - F/P}$$

where F/P and $F/P_{Fab}$ is determined by the equation $$F/P \text{ mole/mole} = \frac{2.8 \times OD_{494}}{P}$$

P = protein
F = fluorescein
$P_{Fab}$ = Fab protein

The following table shows the results of the ratios with varying amounts of hIgG in the reaction mixture.

TABLE III

| Fraction No. | hIgG reacted(mg) | Fab/hIgG mole ratio (n/m) | | | | |
|---|---|---|---|---|---|---|
| | | 0.1 | 0.25 | 0.55 | 1.1 | 2.2 |
| 10 | | 2.26 | 1.5 | 1.5 | 1.5 | 1.5 |
| 11 | | 4.55 | 2.7 | 2.2 | 1.8 | 1.65 |
| 12 | | 4.74 | 2.9 | 2. | 1.44 | 1.34 |
| 13 | | 3.66 | 2.4 | 1.7 | 1.5 | 1.0 |
| 14 | | 2.72 | 2.2 | 1.5 | 1.1 | 0.95 |
| 15 | | | 2.2 | 1.5 | 0.97 | 0.75 |
| 16 | | | 2.9 | 1.8 | 1.22 | 0.82 |
| 17 | | | 5.1 | 3.0 | 2.1 | 1.25 |

EXAMPLE 4

Purification of human Euglobulins

Blue-dextran Sepharose was prepared as described by Wille, Clin. Chim. Acta., 71, 355 (1976). A packed column 0.9×25 cm was prepared from the gel which was degassed before use. After equilibrating the column with an aqueous solution 0.05 M Tris, containing 0.5 M NaCl, 0.05% sodium azide and 0.02 M glycine, at pH 8.0, a euglobulins solution of 3.5 ml, 16.6 mg/ml protein of which about 0.8 mg/ml is IgM by radial immunodiffusion was applied to the column and eluted slowly (1 drop/15 sec.). The collected protein accounted for 60% of the protein applied to the column. The solution was concentrated on an Amicon XM300A down to 1.5 ml which showed 1.25 mg/ml of IgM by radial diffusion and a total of 10 mg/ml protein by UV.

The procedure was repeated using the same column which was regenerated with 6 M urea employing 12 ml of a 1.8 mg/ml IgM solution. The eluted protein peak was collected and concentrated on an Amicon XM50 down to 7 ml. The concentration of IgM by radial diffusion was 2.5 mg/ml.

A different technique was then used for the purification employing a protamine column prepared from protamine sulfate (0.3 g, grade II Sigma) and cyanogen bromide activated Sepharose (15 g) in 50 ml 0.1 M sodium bicarbonate. After incubation overnight, the gel was washed extensively with 0.08 M potassium phosphate containing 0.08 M NaCl and 0.05% sodium azide at pH 7.4 to which was added sufficient NaCl to provide a 1 M solution, followed by using the same potassium phosphate buffer without the additional NaCl. The final gel, about 25 ml when packed was added to a mixture of 65 ml human serum and 65 ml water. After stirring for 4 hrs in the cold, the gel was separated by filtration and washed extensively with the potassium phosphate buffer which had been diluted 1:3 with water. The gel was packed in a column and washed with 0.08 M potassium phosphate buffer, followed by elution of IgM with the same buffer raised to 1 M NaCl and at pH 8. The eluted protein peak was concentrated on Amicon XM50 down to 7.5 ml. The IgM was estimated by radial immunodiffusion as 1.7–1.8 mg/ml.

The procedure was repeated. The column was thoroughly washed with 0.1 M potassium phosphate containing 1 M NaCl and the absorption of 65 ml human serum and elution was repeated as described above. This time, the yield of IgM from the serum was 76% with a purity of about 35% as estimated from radial immunodiffusion and total protein by UV.

EXAMPLE 5

Preparation of Fluorescein-Labeled Fab (FFab(anti(hIgM))) (hIgM = human immunoglobulin M)

To 30 ml of sheep anti-serum containing anti(hIgM) was added solid disodium monoacid phosphate until the pH was 8. The solution was then made 18% in sodium sulfate and stored for 20 min at room temperature. The precipitate was separated by centrifugation and redissolved in 15 ml of 0.1 M potassium phosphate buffer, pH 8. The mixture was centrifuged at room temperature, the solution made 12% in sodium sulfate and the precipitate again collected by centrifugation. The protein was redissolved in 0.1 M sodium acetate buffer pH 5.4, and dialyzed overnight against the same buffer. The resulting solution was clarified by centrifugation (10,000 rpm, 0.5 hr) to a total of about 17 ml of 31 mg/ml protein by UV.

To 3 ml of the above antibody were added cysteine and EDTA to provide a concentration of 2 mM of each and the mixture then incubated with 2.5 mg papain (20 U/ml Sigma) at 37° for 10 hrs. To the mixture was added sodium iodoacetate in water (0.1 ml) so that the final concentration was 2.3 mM. After 1 hr at room temperature, the solution was washed to remove small peptides on Amicon membrane PM10 (mw cwt 10,000) with 0.05 M potassium phosphate buffer, pH 8 (15 ml) and concentrated down to 4 ml. The resulting solution was clarified by centrifugation and was approximately 18.5 mg/ml protein by UV. SDS electrophoresis indicated only a trace amount of undigested IgG.

Two ml of Fab solution were brought to pH 9.0 by the addition of solid sodium carbonate ($Na_2CO_3$). A solution of 1.5 mg of fluorescein isothiocyanate (FITC) in 0.1 ml dry dimethylformamide (DMF) was slowly added (over ½ min.) with stirring at room temperature. After an additional 2 hrs., the solution was briefly clarified on a Brinkmann centrifuge (2½ min.) and applied for separation into a column of Sephadex G-25 (0.9×15 cm) equilibrated with 0.05 M $KPO_4$ buffer at pH 8.0. The yellow protein band (first band eluted) was collected. The final solution was 10.4 mg/ml in protein and degree of labeling 4.1 fluoresceins per Fab.

EXAMPLE 6

Preparation of FFab-hIgM $(Fab)_n$ $(hIgM)_m$ complex a. To 1.5 ml of euglobulins absorbed by blue-Dextran sepharose as described previously was added 0.3 ml of the FFab (anti(hIgM)) solution from Ex. 5 at room temperature and the mixture incubated for an hour. The mixture was then clarified on a Brinkmann centrifuge and separated on Sephadex 4B, employing a 2.4×40 cm column and eluting with 0.1 mole of potassium phosphate buffer containing 0.4 M NaCl, pH 8 in the cold. The flow rate was 1 drop/30–40 sec, 40 drops per tube.

The major portion of the complex was located between fractions 19 and 25.

b. The above procedure was repeated and this time the major portion of the complex was located between fractions 16 and 22. However 50 drops per tube were collected.

EXAMPLE 7

Preparation of Rhodamine Labeled Anti(hIgM)

The antibody solution (0.3 ml, 31 mg/ml) was diluted with 0.12 ml glycerol. The pH was then raised to 10.0 by the addition of solid sodium carbonate ($Na_2CO_3$) and immediately lowered to 9.3 by the addition of solid sodium bicarbonate ($NaHCO_3$). A solution of 0.8 mg of tetramethylrhodamine isothiocyanate in 80 μl dry dimethylformamide was added with stirring. After 3 hrs. at room temperature the solution was briefly clarified on a Brinkmann centrifuge (2½ min.) and applied for separation to a column of Sephadex LH-20 (0.9×10 cm). The column is equilibrated with a buffer consisting of 7 parts of 0.04 M $KPO_4$ buffer at pH 8.0 and 3 parts of glycerol. The red protein band (first band eluted) was collected in 0.8 ml.

In order to demonstrate the subject invention a number of assays were carried out. In the first assay, the complex of FFab((anti(hIgG)) with hIgG was titrated with rhodamine labeled antihIgG (R anti(hIgG)) (See U.S. Pat. No. 3,996,345, Ex. IV, Col. 27) in accordance with the following protocol. The buffer employed was 0.01 M PBS, pH 8.0 (0.05% $NaN_3$; 2% PEG6000). The complex was diluted 1:8 with buffer. The rhodamine labeled anti(hIgG) was serially diluted. The assay mixture was prepared by combining 25 μl of the diluted complex, 25 μl of the rhodamine labeled anti(hIgG) and 500 μl of the buffer to provide a final concentration of hIgG of $\sim 1.08 \times 10^{-3}$ mg/ml and the mixture incubated at room temperature for 15 min. Readings were then made. The following are the results.

TABLE IV

| R anti(hIgG) Dilution | Relative Fluorescence |
| --- | --- |
| 1:6 | 37 |
| 1:8 | 40 |
| 1:10 | 42 |
| 1:20 | 54 |
| 1:40 | 76 |
| (no R anti(hIgG) | 100 |

Following the procedure described above, an assay for hIgG was performed. The R anti(hIgG) was diluted 1:14 with water. A solution of hIgG (Pentex, 0.857 mg/ml by uv) was serially diluted. To the assay solution described previously was added 25 μl of the serially diluted hIgG sample in 250 μl buffer to provide a total assay volume of 825 μl. The following are the results.

TABLE V

| hIgG dilutions | Relative Fluorescence |
| --- | --- |
| 1:240 | 51 |
| 1:120 | 53 |
| 1:60 | 58 |
| 1:30 | 68 |
| 1:15 | 79 |
| 1:8 | 86 |
| 1:4 | 93 |
| 1:2 | 98 |
| no R anti(hIgG) | 100 |
| no hIgG | 49 |

For the determination of IgM, the R anti(hIgG) was diluted with water. The titration procedure described previously was employed to provide a total volume of 550 μl. The following are the results.

TABLE VI

| R anti(hIgM) dilutions | Relative Fluorescence |
| --- | --- |
| 1:5 | 30 |
| 1:10 | 33 |
| 1:20 | 42 |

TABLE VI-continued

| R anti(hIgM) dilutions | Relative Fluorescence |
|---|---|
| no R anti(hIgM) | 100 |

Following the previously described assay procedure an hIgM solution obtained from a protamine column treatment (4 mg/ml hIgM) was serially diluted. Then, the serially diluted hIgM was combined with one of the fractions of the complex of Ex. 6. The R anti(hIgM) was diluted 1:8. The following are the results.

| Concentration of hIgM after dilution, mg/ml | Relative Fluorescence |
|---|---|
| 0 | 51 |
| 0.03 | 52 |
| 0.08 | 54 |
| 0.16 | 59 |
| 0.32 | 61 |
| 0.64 | 73 |
| 1.28 | 81 |
| 2.56 | 88 |
| no R anti(hIgM) | 100 |

The subject method provides for a simple effective procedure for providing labeled reagents for competitive protein binding assays substantially free of label which could interfere with the sensitivity of the assay by providing a large background signal or varying responses unrelated to the amount of analyte present.

In addition, one can establish a common protocol for conjugating labels to Fab fragments which can be used with a wide variety of analytes. By employing a complex of a labeled Fab fragment with a ligand analyte as the labeled ligand, substantial flexibility is achieved in the ratio of label to ligand. Furthermore, relatively simple purification techniques can be employed to separate labeled ligand from extraneous labeled protein. Thus, assay sensitivity can be greatly enhanced by the reduction in background signal.

Although the foregoing invention has been described in some detail by way of illustration and example for purposes of clarity of understanding, it will be obvious that certain changes and modifications may be practiced within the scope of the appended claims.

What is claimed is:

1. A method for performing a protein binding assay employing a labeled ligand complex reagent, where the ligand is a protein and a member of a specific binding pair consisting of ligand and antiligand and is polyepitopic and of at least about 15,000 molecular weight; and said label is of from about 100 to 2,000 molecular weight and provides a detectible signal affected by the proximity of antiligand due to the steric bulk of said antiligand or a group conjugated to said antiligand which interacts with said label;

said labeled ligand complex reagent prepared by the method comprising:
 (a) combining said ligand with a γ-globulin composition containing Fab fragments derived from antiligand, said R-globulin composition having been conjugated with said label, wherein said ligand and labeled fab fragments form complexes having at least one free ligand epitopic site; and
 (b) separating said complexes from other labeled protein;

said protein binding assay comprising;
combining said complexes with a sample suspected of containing said ligand in an assay medium for determination of said ligand.

2. A method according to claim 1 wherein said label is a fluorescer.

3. A method according to claim 1, wherein said protein ligand is a globulin.

4. A method according to claim 3 wherein said label is a chemiluminescer.

5. A method for performing a protein binding assay for immunoglobulin employing a labeled immunoglobulin complex reagent wherein said label is of from about 100 to 2,000 molecular weight and provides a detectible signal affected by the proximity of antiimunoglobulin due to the steric bulk of said antiimmunoglobulin or a group conjugated to said antiimmunoglobulin which interacts with said label;

said labeled immunoglobulin complex reagent prepared by the method comprising:
 (a) combining said immunoglobulin with a γ-globulin composition containing Fab fragments derived from a serum protein composition having antiimmunoglobulin and other protein conjugated with said label, wherein said Fab fragments derived from antiimmunoglobulin and said immunoglobulin form complexes having at least one free ligand epitopic site; and
 (b) separating said complexes from the other labeled protein;

said protein binding assay comprising:
combining said complexes with a sample suspected of containing said immunoglobulin in an assay medium for determination of said immunoglobulin.

6. A method according to claim 5, wherein said immunoglobulin is IgG.

7. A method according to claim 5, wherein said immunoglobulin is IgM.

8. A method according to claim 5, wherein said immunoglobulin is IgA.

9. A method according to claim 5, wherein said immunoglobulin IgE.

10. A method according to any one of claims 5 to 9, wherein said label is a fluorescer.

* * * * *